US008600509B2

(12) United States Patent
McDonald et al.

(10) Patent No.: US 8,600,509 B2
(45) Date of Patent: Dec. 3, 2013

(54) LEAD SPLITTER FOR AN ELECTRICAL STIMULATION SYSTEM AND SYSTEMS AND METHODS FOR MAKING AND USING

(71) Applicant: Boston Scientific Neuromodulation Corporation, Valencia, CA (US)

(72) Inventors: Matthew Lee McDonald, Pasadena, CA (US); Joshua Dale Howard, North Hollywood, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 13/764,251

(22) Filed: Feb. 11, 2013

(65) Prior Publication Data

US 2013/0150907 A1 Jun. 13, 2013

Related U.S. Application Data

(62) Division of application No. 12/533,223, filed on Jul. 31, 2009, now Pat. No. 8,374,695.

(51) Int. Cl.
*A61N 1/00* (2006.01)

(52) U.S. Cl.
USPC .................... 607/37; 607/2; 607/36; 607/115

(58) Field of Classification Search
USPC .......................................... 607/2, 36–37, 115
See application file for complete search history.

(56) References Cited

U.S. PATENT DOCUMENTS

| | | | |
|---|---|---|---|
| 4,402,329 A | 9/1983 | Williams |
| 4,444,195 A | 4/1984 | Gold |
| 5,144,960 A | 9/1992 | Mehra et al. |
| 5,417,719 A | 5/1995 | Hull et al. |
| 5,676,694 A | 10/1997 | Boser et al. |
| 5,797,970 A | 8/1998 | Pouvreau |
| 5,800,465 A | 9/1998 | Thompson et al. |
| 6,038,463 A | 3/2000 | Laske et al. |
| 6,078,839 A | 6/2000 | Carson |
| 6,772,015 B2 | 8/2004 | Dahl et al. |
| 6,937,897 B2 | 8/2005 | Min et al. |
| 7,120,502 B2 | 10/2006 | Tuominen |
| 7,128,600 B2 | 10/2006 | Osypka |
| 2004/0260355 A1 | 12/2004 | Holleman et al. |

OTHER PUBLICATIONS

U.S. Appl. No. 12/533,223, Official Communication mailed May 14, 2012.

*Primary Examiner* — Nicole F Lavert
(74) *Attorney, Agent, or Firm* — Frommer Lawrence & Haug LLP; Patrick R. Turner

(57) ABSTRACT

A splitter for an electrical stimulation system includes a junction having a proximal end and a distal end. An elongated proximal member extends from the proximal end of the junction. The proximal member includes a plurality of terminals disposed on a proximal end of the proximal member. A plurality of elongated distal members extend from the distal end of the junction. Each distal member includes a connector disposed on a distal end of the distal member. The connector is configured and arranged for receiving a lead or lead extension. One of the distal members is longitudinally aligned with the proximal member and at least another one of the distal members is longitudinally offset from the proximal member. A plurality of conductors couple the terminals of the proximal member to the connectors of the distal members.

20 Claims, 11 Drawing Sheets

LEAD SPLITTER FOR AN ELECTRICAL STIMULATION SYSTEM AND SYSTEMS AND METHODS FOR MAKING AND USING

This utility patent application is a divisional of U.S. patent application Ser. No. 12/533,223, which is now U.S. Pat. No. 8,374,695, issued Feb. 11, 2013, which is incorporated herein by reference.

FIELD

The present invention is directed to the area of implantable electrical stimulation systems and methods of making and using the systems. The present invention is also directed to implantable electrical stimulation systems having lead splitters for coupling a plurality of leads (or lead extensions) to a single connector, as well as methods of making and using the leads, lead splitters, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a splitter for an electrical stimulation system includes a junction having a proximal end and a distal end. An elongated proximal member extends from the proximal end of the junction. The proximal member includes a plurality of terminals disposed on a proximal end of the proximal member. A plurality of elongated distal members extend from the distal end of the junction. Each distal member includes a connector disposed on a distal end of the distal member. The connector is configured and arranged for receiving a lead or lead extension. One of the distal members is longitudinally aligned with the proximal member and at least another one of the distal members is longitudinally offset from the proximal member. A plurality of conductors couple the terminals of the proximal member to the connectors of the distal members. Each connector is coupled to a different subset of the terminals using the plurality of conductors. Each terminal of the proximal member is coupled by at least one of the conductors to a connector of only one of the plurality of elongated distal members.

In another embodiment, an electrical stimulation system includes a splitter, a control module, and a connector. The splitter includes a junction having a proximal end and a distal end. An elongated proximal member extends from the proximal end of the junction. The proximal member includes a plurality of terminals disposed on a proximal end of the proximal member. A plurality of elongated distal members extend from the distal end of the junction. Each distal member includes a connector disposed on a distal end of the distal member. The connector is configured and arranged for receiving a lead or lead extension. One of the distal members is longitudinally aligned with the proximal member and at least another one of the distal members is longitudinally offset from the proximal member. A plurality of conductors couple the terminals of the proximal member to the connectors of the distal members. Each connector is coupled to a different subset of the terminals using the plurality of conductors. Each terminal of the proximal member is coupled by at least one of the conductors to a connector of only one of the plurality of elongated distal members. The control module is configured and arranged to electrically couple to the splitter. The control module includes a housing and an electronic subassembly disposed in the housing. The connector is configured and arranged for receiving the proximal member of the splitter. The connector has a proximal end, a distal end, and a longitudinal length. The connector includes a connector housing defining a port at the distal end of the connector. The port is configured and arranged for receiving the proximal end of the splitter. The connector also includes a plurality of connector contacts disposed in the connector housing. The connector contacts are configured and arranged to couple to at least one of the plurality of terminals disposed on the proximal end of the splitter.

In yet another embodiment, a method for electrically stimulating patient tissue includes inserting a distal end of at least two leads into a patient. The distal ends of each of the leads include a plurality of electrodes. The proximal ends of each of the leads are coupled to a splitter. The splitter includes a junction having a proximal end and a distal end. An elongated proximal member extends from the proximal end of the junction. The proximal member includes a plurality of terminals disposed on a proximal end of the proximal member. A plurality of elongated distal members extend from the distal end of the junction. Each distal member includes a connector disposed on a distal end of the distal member. The connector is configured and arranged for receiving a lead or lead extension. One of the distal members is longitudinally aligned with the proximal member and at least another one of the distal members is longitudinally offset from the proximal member. A plurality of conductors couple the terminals of the proximal member to the connectors of the distal members. Each connector is coupled to a different subset of the terminals using the plurality of conductors. Each terminal of the proximal member is coupled by at least one of the conductors to a connector of only one of the plurality of elongated distal members. The terminals disposed on the proximal member of the splitter are coupled to a connector of a control module. Electrical signals are generated by the control module for stimulating patient tissue via the electrodes disposed on each of the at least two leads.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems having lead splitters for coupling a plurality of leads (or lead extensions) to a single connector, as well as methods of making and using the leads, lead splitters, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and U.S. Patent Application Publication Nos. 2005/0165465 and 2007/0150036, all of which are incorporated by reference.

Figure 1:
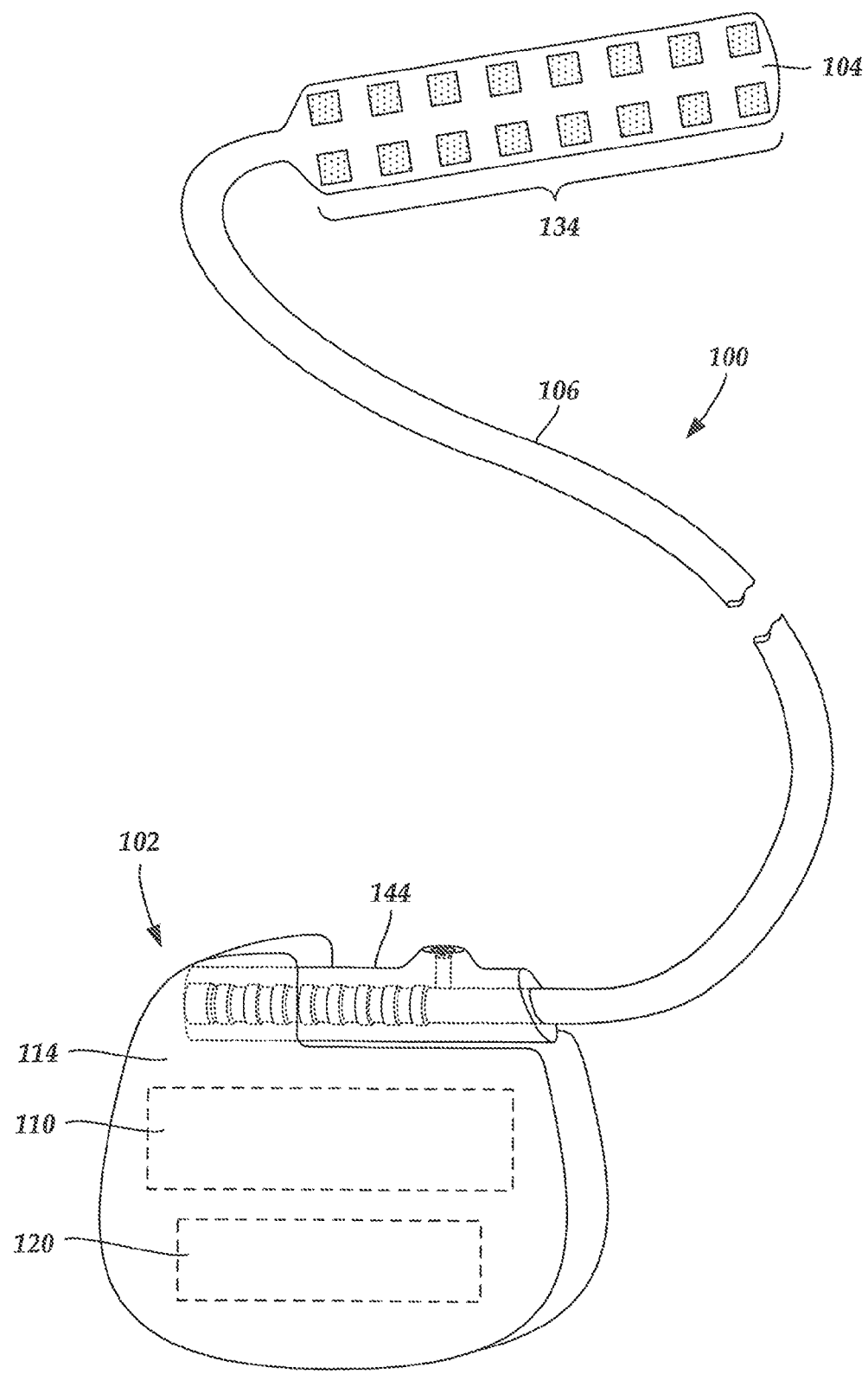
FIG. 1 is a schematic view of one embodiment of an electrical stimulation system, according to the invention.
Figure 2:
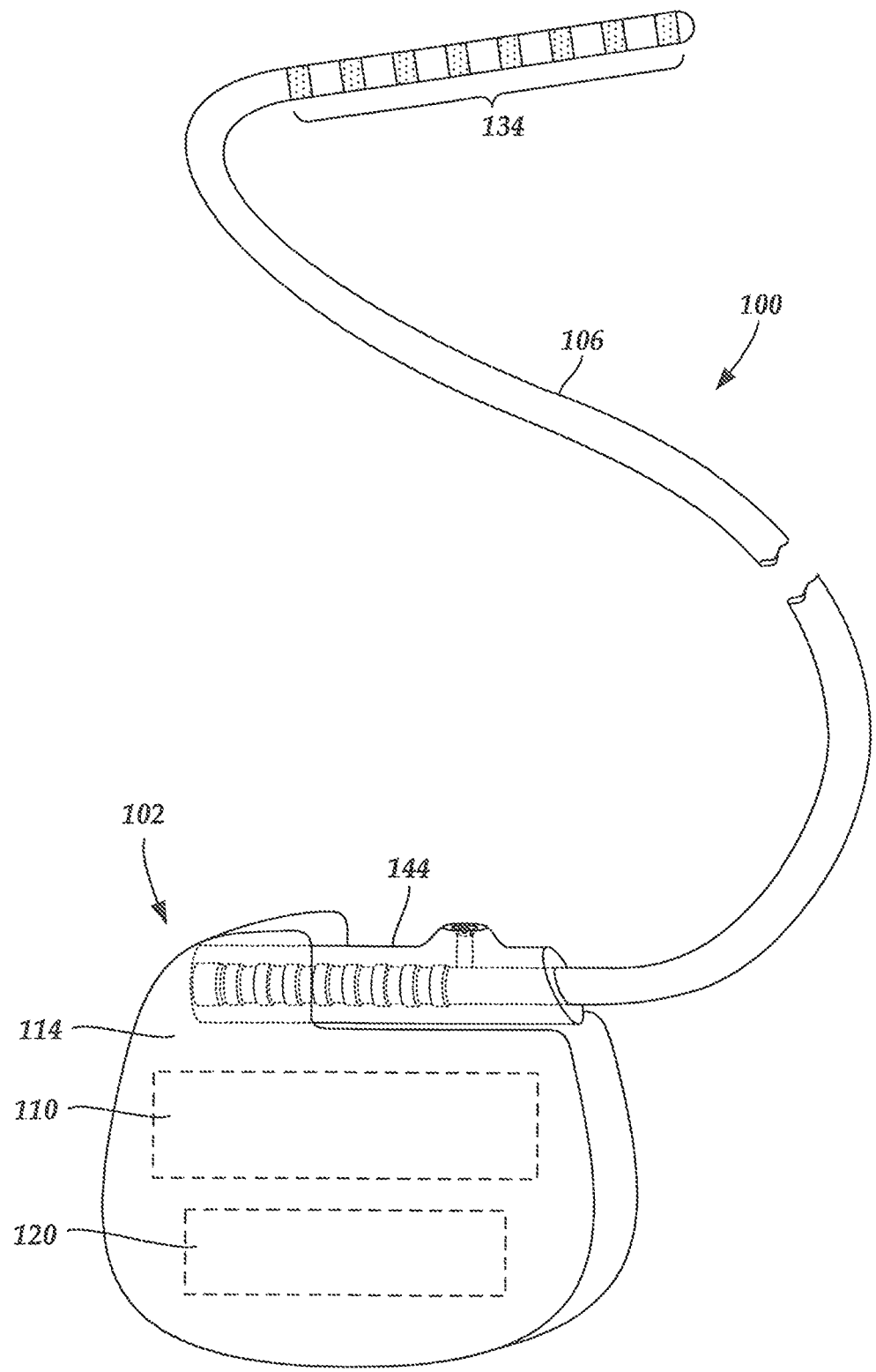
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone, epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding connector contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductors may be embedded in the non-conductive material of the lead or can be disposed in one or more lumens (not shown) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
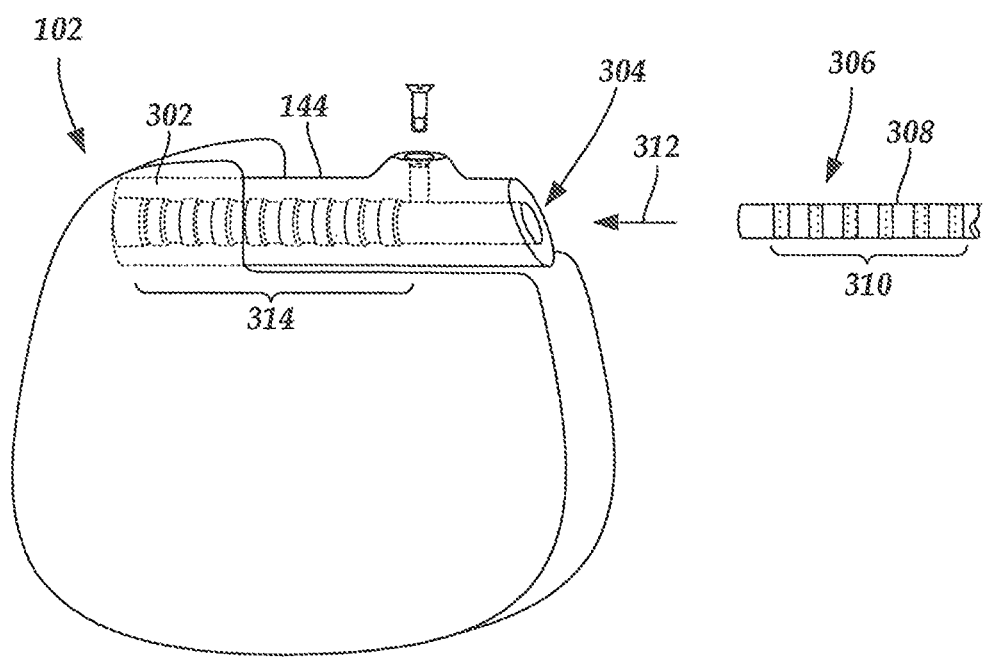
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. Nos. 7,244,150 and 8,224,450, which are incorporated by reference.

Figure 3B:
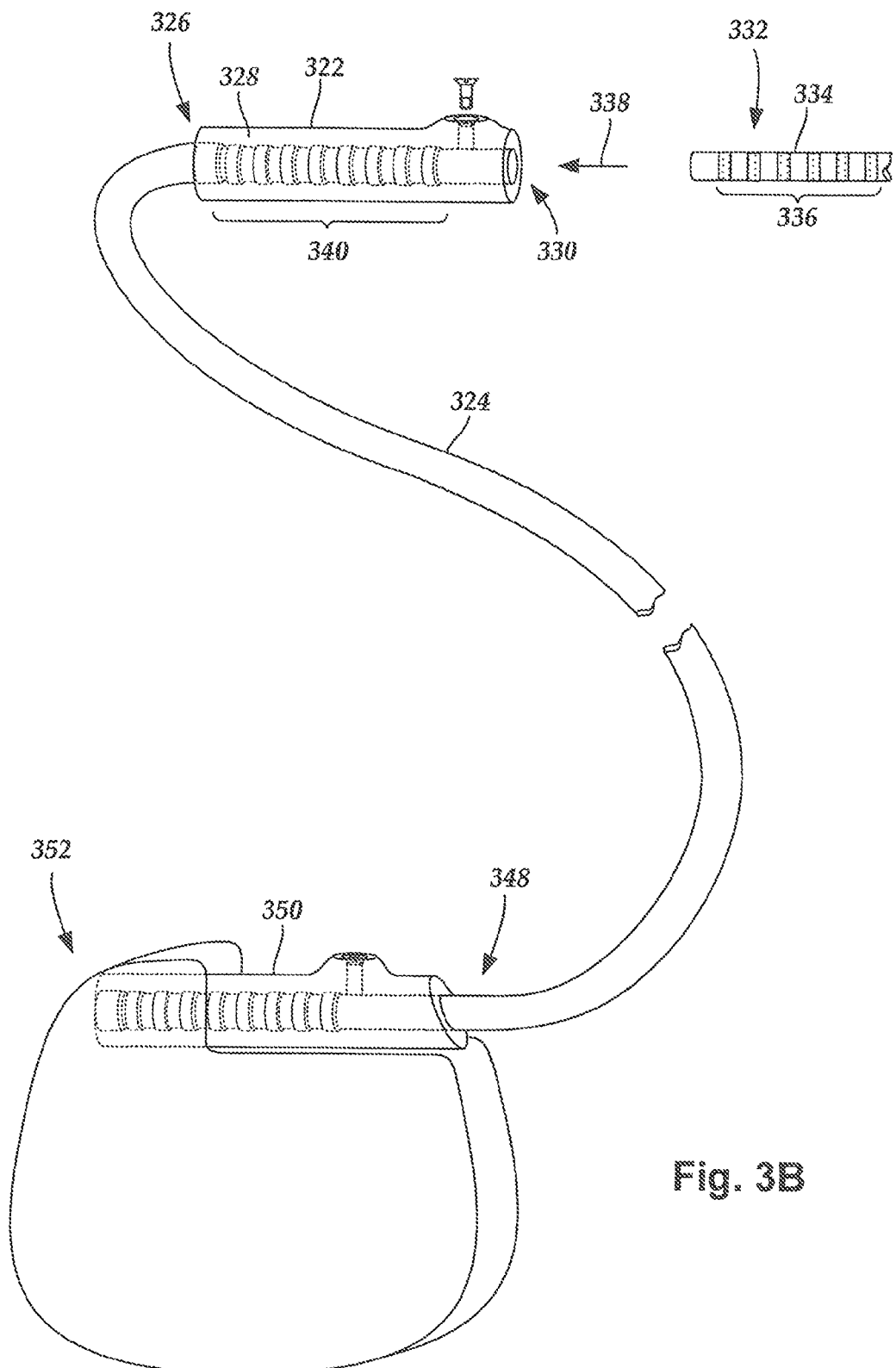
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductors (not shown) that electrically couple the connector contacts 340 to a proximal end 348 of the lead extension 324 that is opposite to the distal end 326. In at least some embodiments, the conductors disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Providing effective therapeutic treatment for a patient may sometimes require stimulation at two or more target sites. Two or more leads may be used to effectively provide stimulation at each of the target sites. Connectors (e.g., connectors disposed on control modules, implantable pulse generators, lead extensions, or the like) have a limited number of ports into which leads (or lead extensions) may be inserted. It may be the case that the number of target sites exceeds the number of ports in the connector. In which case, it may be necessary to implant additional devices into the patient to provide enough ports for each of the leads.

A splitter may be used to electrically couple multiple leads (or lead extensions) to conductive contacts disposed in a single port of a connector, for example, a single port of an implantable pulse generator. The splitter includes a proximal member having terminals configured and arranged for insertion into an external connector (e.g., a connector disposed on a control module, an implantable pulse generator, a lead extension, or the like) and two or more distal members each having connectors configured and arranged for coupling to terminals disposed on elongated members (e.g., leads, lead extensions, or the like). Conductors are routed in the splitter from the terminals of the proximal member to the connectors of the distal members. In at least some embodiments, at least one conductor extends from each of the connectors of the distal members to at least one of the terminals of the proximal member.

One end of the splitter may be inserted into a port defined in the external connector. In at least some embodiments, electric signals generated by a coupled control module may be output from the port of the external connector, transmitted along the splitter, and output to two or more leads coupled to the connectors disposed on the distal members. In at least some embodiments, the electric signals are output from the splitter to one or more intervening devices (e.g., one or more lead extensions) between the splitter and the leads.

In at least some embodiments, the connectors are configured and arranged to receive the same type of lead (or lead extension) as one another. In at least some embodiments, the splitter is not an adapter. In other words, in at least some embodiments each of the connectors disposed on the distal members are configured and arranged to receive terminals that are disposed on leads (or lead extensions) and that are arranged in a similar configuration to the terminals disposed on the proximal member. In at least some embodiments, each subset of terminals of the proximal end is coupled to one or more connector contacts disposed on only one of the connectors. For example, a first subset of terminals may couple to a first connector without coupling to a second connector, and a second subset of terminals may couple to the second connector without coupling to the first connector.

Figure 4:
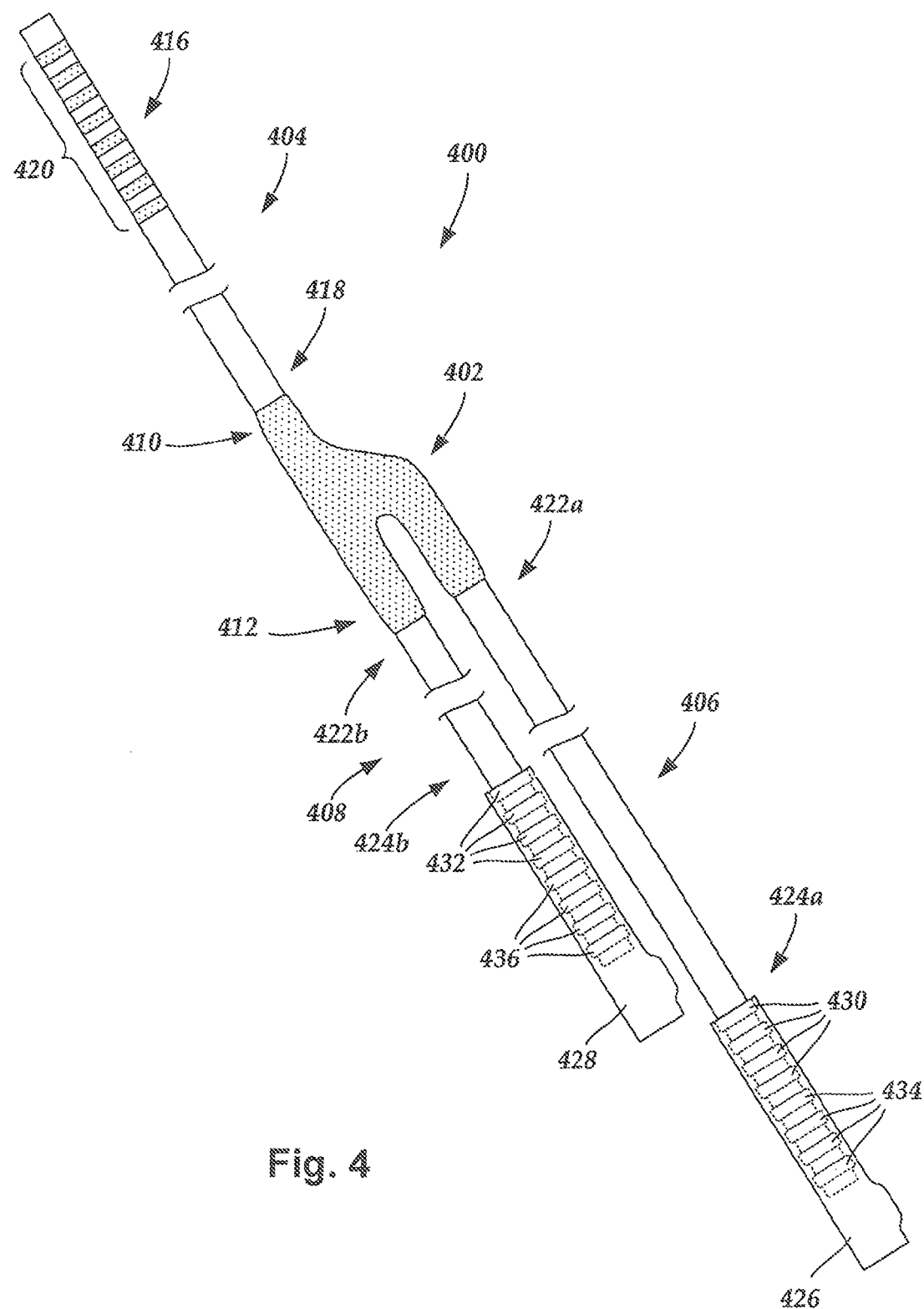
FIG. 4 is a schematic side view of one embodiment of a splitter for an electrical stimulation system, according to the invention.

FIG. 4 is a schematic side view of one embodiment of a splitter 400. The splitter 400 includes a junction 402 coupling an elongated proximal member 404 to elongated distal members 406 and 408 via the junction 402. The junction 402 includes a proximal end 410 and a distal end 412.

The proximal member 404 has a proximal end 416 and a distal end 418. The proximal end 416 includes terminals 420 and the distal end extends into the proximal end 410 of the junction 402. Each of the distal members 406 and 408 has a proximal end 422a and 422b, respectively, and a distal end 424a and 424b, respectively. The proximal ends 422a and 422b of the distal members 406 and 408, respectively, extend into the distal end 412 of the junction 402. The distal ends 424a and 424b of the distal members 406 and 408, respectively, each include a connector 426 and 428, respectively. Connector contacts 430 and 432 are disposed in connectors 426 and 428, respectively.

In at least some embodiment, one of the distal members 406 or 408 is longer in length than the other of the distal members 406 or 408. In at least some embodiments, the connectors 426 and 428 are configured and arranged such that, when the distal members 406 and 408 are extended in substantially straight orientations, the connectors 426 and 428 are axially staggered from one another.

In at least some embodiments, when the distal members 406 and 408 are extended in substantially straight orientations, the connectors 426 and 428 are axially staggered from one another such that the connectors 426 and 428 do not overlap one another. It may be an advantage to not have the connectors 426 and 428 overlap in order to reduce the profile of the splitter 400 during insertion or implantation of the splitter 400, thereby potentially reducing invasiveness associated with implantation of the splitter 400. Another advantage of reducing the profile of the splitter 400 may be a potential increase in available implantation locations. A further advantage may be that a health care professional may utilize the different lengths of the distal members 406 and 408 to distinguish between the leads to which the connectors 426 and 428 are coupled.

Any number of distal members can be used including, two, three, four, five, six, seven, eight, nine, ten, eleven, twelve, thirteen, fourteen fifteen, sixteen, or more distal members. It will be understood that other numbers of distal members may be used as well.

In at least some embodiments, the proximal member 404 is longitudinally aligned with one of the distal members 408. In at least some embodiments, the proximal member 404 is longitudinally offset from one or more of the other distal members 406. In at least some embodiments, the proximal member 408 is coupled to the longitudinally aligned distal member 408. In at least some embodiments, the proximal member 404 is continuous with the longitudinally aligned distal member 408.

In at least some embodiments, when the splitter 400 includes two distal members, the junction 402 is h-shaped. For example, as shown in FIG. 4, the upper left (straight) portion of the h-shaped junction 402 receives the proximal member 404, the lower left (straight) portion of the h-shaped junction 402 receives the longitudinally aligned distal member 408, and the lower right (curved) portion of the h-shaped junction 402 receives the longitudinally offset distal member 406. In at least some embodiments, the splitter 400 may include a plurality of h-shaped junctions 402. For example, in at least some embodiments one or more distal portions of a first "h" may form a proximal portion of a second "h."

It may be an advantage to use an h-shaped configuration because one length of continuous material can extend through the junction, thereby potentially increasing the strength of the junction. A further advantage to having a length of continuous material extend through the junction is that a continuous lumen may be defined within the length of material through which one or more devices may extend (e.g., a stylet or the like).

In at least some embodiments, the proximal member 404 is configured and arranged for insertion into an external connector (e.g., a connector disposed on a control module, a lead extension, or the like). In at least some embodiments, the terminals 420 of the proximal member 404 are configured and arranged to electrically couple with connector contacts disposed in the external connector. In at least some embodiments, conductors disposed in the splitter 400 are electrically coupled to the terminals 420. In at least some embodiments, the conductors electrically couple the terminals 420 to the connector contacts 430 and 432 disposed in the connectors 426 and 428, respectively.

In at least some embodiments, each of the terminals 420 is coupled to one or more connector contact 430 or 432 disposed in one of the connectors 426 or 428 without coupling to any of the connector contacts 430 or 432 disposed on the other of the connectors 426 or 428. In at least some embodiments, each conductor couples one of the terminals 420 to one of the connector contacts 430 and 432 disposed in one of the connectors 426 or 428, respectively. Accordingly, in at least some embodiments, the number of conductors disposed in the proximal member 404 is equal to the number of terminals 420. Also, in at least some embodiments, the collective number of connector contacts 430 and 432 coupled to conductors is equal to the number of terminals 420. In at least some embodiments, the number of connector contacts 430 disposed in the connector 426 and coupled to the conductors is equal to the number of connector contacts 432 disposed in the connector 428 and coupled to the conductors.

For example, in at least some embodiments, when the splitter 400 includes eight terminals 420, four connector contacts 430 disposed in the connector 426 are coupled to conductors, and four connector contacts 432 disposed in the connector 428 are coupled to conductors. In FIG. 4, the proximal-most four connector contacts 430 and 432 of connectors 426 and 428, respectively, are coupled to conductors. In at least some embodiments, one or more of the connectors 426 and 428 include one or more regions 434 and 436, respectively, that may include one or more connector contacts that are not coupled to conductors or one or more spacers that are formed from non-conductive material (e.g., one or more thermoplastics, or the like). In FIG. 4, the regions 434 and 436 are shown as conductors that are not coupled to conductors.

As discussed below with reference to FIGS. 8C-11, the connector contacts that are coupled to the conductors can be arranged in any configuration within the connectors 426 and 428, and are not limited to being the proximal-most connector contacts. For example, the connector contacts that are coupled to the conductors can be the distal-most connector contacts, some or all of the middle connector contacts, the distal-most and the proximal-most connectors, every other connector contact, or the like or combinations thereof.

Figure 5:
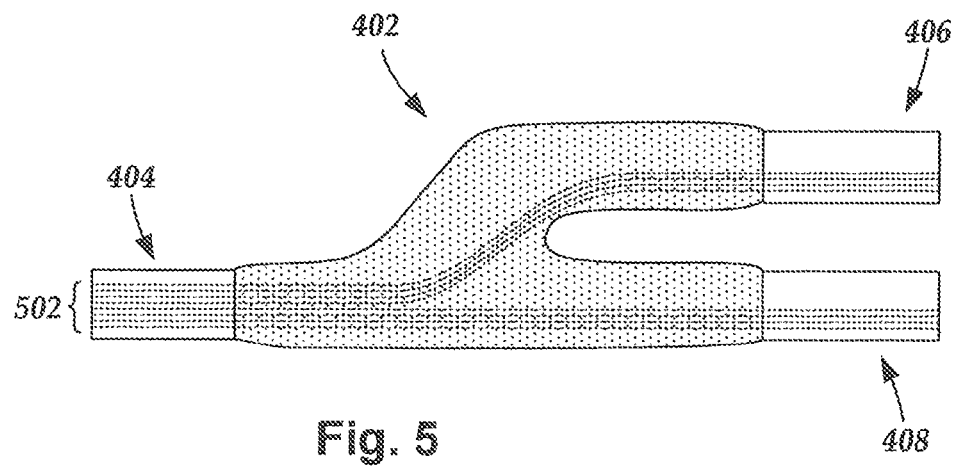
FIG. 5 is a schematic close-up side view of one embodiment of a junction of the splitter of FIG. 4 and the routing of conductors through the junction, according to the invention.

FIG. 5 is a schematic close-up side view of one embodiment of the junction 402. The junction 402 receives the proximal member 404 and the distal members 406 and 408. Conductors 502 extending along the proximal member 404 are routed at the junction 402 such that at least one of the conductors 502 is routed along the distal member 406, and at least one of the conductors 502 is routed along the distal member 408.

Any number of conductors 502 may extend along the proximal member 404 including, for example, two, three, four, five, six, seven, eight, nine, ten, eleven, twelve, fourteen, sixteen, or more conductors 502. It will be understood that other numbers of conductors 502 may extend along the proximal member 404 as well.

It will also be understood that the conductors 502 extending along the proximal member 404 may be distributed between distal members 406 and 408 in any proportion. In at least some embodiments, each of the connectors 426 and 428 include an equal number of conductors coupled to connector contacts 430 and 432, respectively. In at least some embodiments, eight conductors 502 extend along the proximal member 404 and are routed at the junction 402 such that four of the eight conductors 502 extend along the distal member 406 and the remaining four of the eight conductors 502 extend along the distal member 408.

Figure 6:
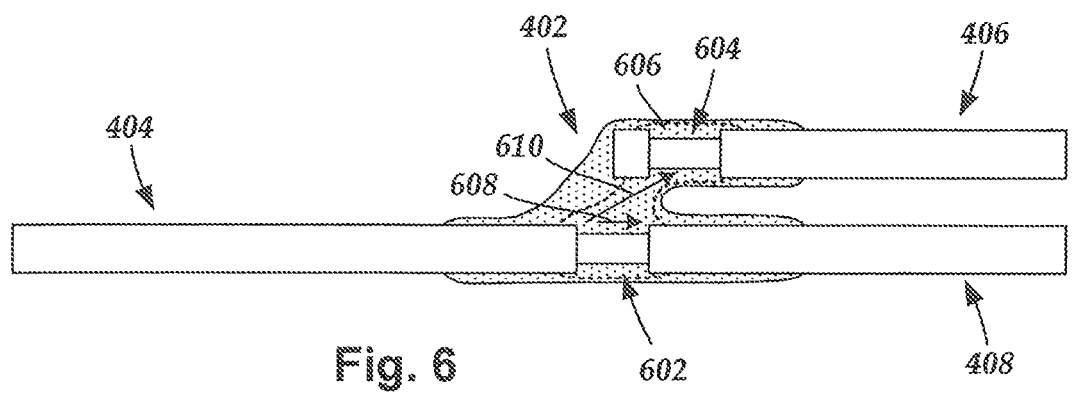
FIG. 6 is a schematic longitudinal cross-sectional view of one embodiment of the junction of FIG. 5 housing a portion of a proximal member and portions of a plurality of distal members, one of the distal members longitudinally aligned and continuous with the proximal member, according to the invention.

FIG. 6 is a schematic longitudinal cross-sectional view of one embodiment of the junction 402 receiving the proximal member 404 and the distal members 406 and 408. The proximal member 404 is longitudinally aligned with the distal member 408. The distal member 408 includes a removed section 602 disposed in the junction 402 for providing access to at least one of the conductors disposed in the distal member 406. Likewise, the distal member 406 includes a removed section 604 disposed in the junction 402. Hereinafter, when the proximal member 404 is continuous with the distal member 408, the removed section 602 is considered to be disposed on the distal member 408, not on the proximal member 404, for consistency of explanation.

In at least some embodiments, the junction 402 defines a cavity 606, shown in FIG. 6 as being defined by dotted lines. In at least some embodiments, the removed sections 602 and 604 are disposed in the junction 402 such that the removed sections 602 and 604 are disposed in the cavity 606. Thus, conductors extending from the proximal member 404 may, within the junction 402, either continue to extend along the distal member 408, as shown by directional arrow 608, or may extend across the cavity 606 to the removed section 604 and into the distal member 406, as shown by directional arrow 610.

The junction 402 may be formed from any biocompatible material suitable for implantation into a patient. In at least some embodiments, the junction 402 is formed using a molding process. In at least some embodiments, the junction 402 is a unitary structure. In at least some embodiments, the cavity 606 is fluid tight. In at least some embodiments, the cavity 606 may be filled with one or more substances (e.g., silicone, or the like).

Figure 7A:
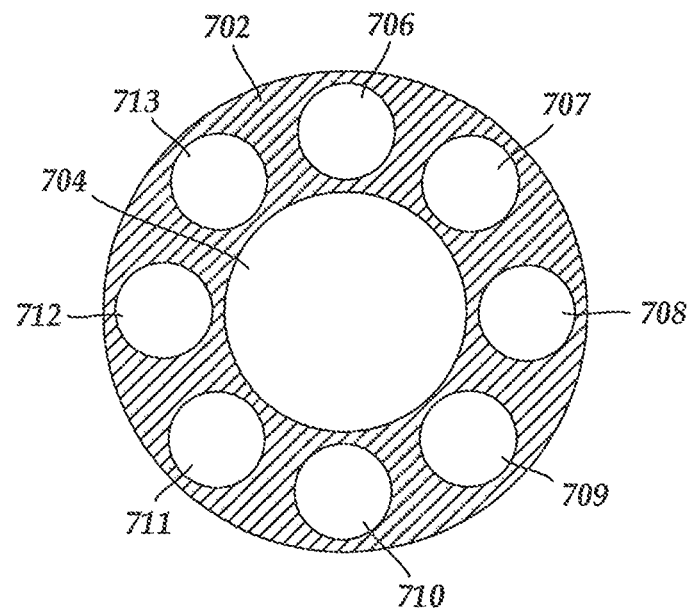
FIG. 7A is a schematic transverse cross-sectional view of one embodiment of a body of a proximal member or a distal member suitable for use with a junction to form a splitter, the body defining a plurality of lumens arranged in an exemplary configuration, according to the invention.

Conductors may be disposed within the proximal member 404, the distal member 406, and the distal member 408 in any number of different arrangements. FIG. 7A is a schematic end view of one embodiment of a body 702 extending from a proximal end to a distal ends of one or more of the proximal member (404 of FIG. 4), the distal member (406 of FIG. 4), or the distal member (408 of FIG. 4). The body 702 defines multiple lumens. For example, in FIG. 7A, and in other figures, the body 702 defines a central lumen 704 and conductor lumens 706-713. It will be understood that some embodiments may not include the central lumen 704. In at least some embodiments, one or more of the proximal member (404 of FIG. 4), the distal member (406 of FIG. 4), or the distal member (408 of FIG. 4) may additionally include one or more layers of material disposed over the body 702.

Figure 7B:
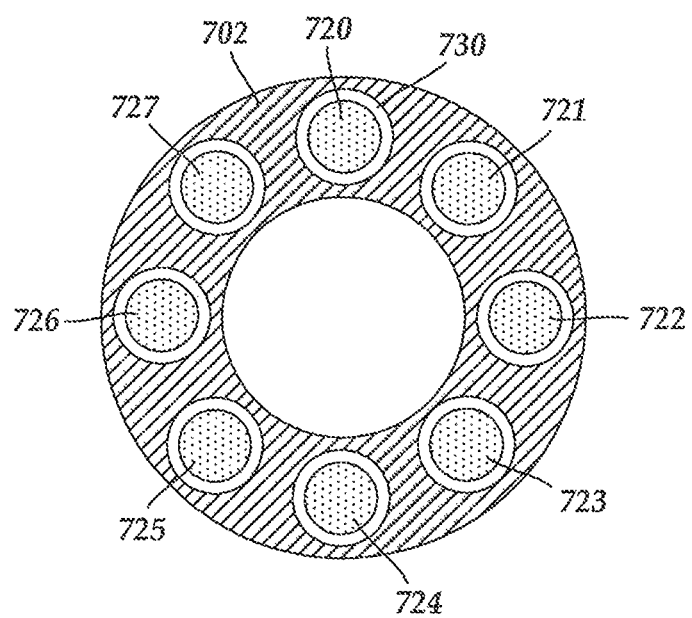
FIG. 7B is a schematic transverse cross-sectional view of one embodiment of conductors disposed in lumens of the body of FIG. 7A, according to the invention.

In at least some embodiments, one or more conductors extend along at least a portion of a longitudinal length of the body 702 within one of the conductor lumens 706-713. FIG. 7B is a schematic end view of one embodiment of the conductors 720-727 disposed in the body 702. In at least some embodiments, insulation 730 is disposed around a longitudinal length of one or more of the conductors 720-727. In FIG. 7B, the conductors 720-727 are shown as being single-filar. It will be understood that one or more of the conductors 720-727 may be multi-filar. For example, in at least some embodiments, one or more of the conductors 720-727 is 16-filar. In at least some embodiments, when one or more of the conductors 720-727 are multi-filar, insulation may be disposed individually over one or more of the filaments in addition to, or instead of, around the collective number of filaments that form the one or more conductors 720-727.

Ends of the conductors 720-727 extend from the end of the body 702. The extending ends of the conductors 720-727 on one end of the body 702 are coupled to terminals (e.g., terminals 420) and the extending ends of the conductors 720-727 on the other end of the body 702 are coupled to connector contacts (e.g., connector contacts 416 or 418) disposed in connectors (e.g., connectors 426 or 428). It will be understood that conductors may extend along bodies with different lumen arrangements, as well as bodies that do not define lumens at all. In some embodiments, one or more lumens may house multiple conductors. In some embodiments, one or more lumens may not house any conductors.

Figure 8A:
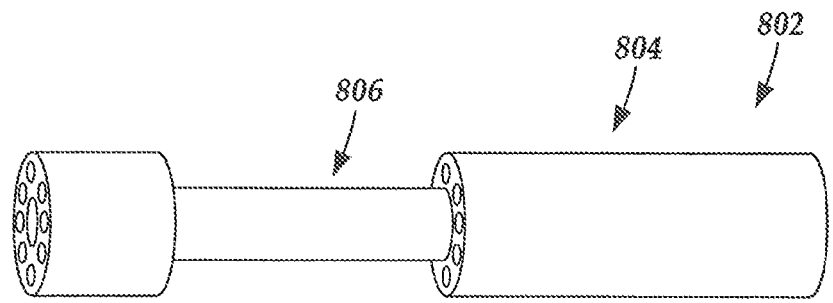
FIG. 8A is a schematic perspective close-up view of one embodiment of a portion of a distal member having a lumen configuration similar to the lumen configuration of FIG. 7A, the distal member having lumens exposed through a removed section, according to the invention.

FIG. 8A is a schematic perspective close-up view of one embodiment of a portion of a distal member 802 that is longitudinally aligned with a proximal member (see e.g., proximal member 404 of FIG. 4). The distal member 802 includes a body 804 with a removed section 806. The removed section 806 is formed by the removal of an outer portion of the body 804 (as well as any overlying layers of material, if applicable) at a desired location along the length of the body 804. In at least some embodiments, the removed section 806 is formed by an ablation process (e.g., laser ablation, or the like).

The removed section 806 of the body 804 exposes one or more lumens, at least some of which are configured and arranged to receive one or more conductors. In at least some embodiments, the removed section 806 is formed by skiving the body 804. In at least some embodiments, the removed section 806 is formed as one or more access ports through the body 804. In at least some embodiments, the removed section 806 is formed as a transverse channel extending at least partially around a circumference of the body 804. It will be understood that a plurality of removed sections 806 may be formed in at least one of the distal members. In at least some embodiments, the transverse channel forms a mechanical interlock between the distal member and the junction (402 in FIG. 4). The mechanical interlock may increase the mechanical retention force on the distal member. In at least some embodiments, the material from which the junction is formed may flow into or around the section.

Figure 8B:
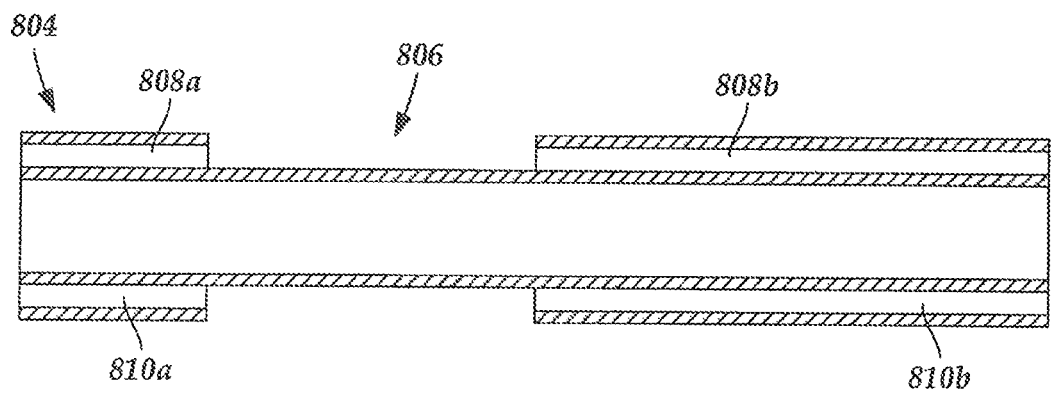
FIG. 8B is a schematic longitudinal cross-sectional view of one embodiment of the portion of the distal member of FIG. 8A, according to the invention.

FIG. 8B is a schematic longitudinal cross-sectional view of one embodiment of the removed section 806 of the body 804 of the distal member 802 longitudinally aligned with a proximal member (see e.g., proximal member 404 of FIG. 4). The body 804 defines a number of conductor lumens, such as conductor lumens 808a, 808b, 810a and 810b, each of which are exposed by the removed section 806 of the body 804. It will be understood that the number or positioning of the lumens exposed by the removed section 806 may vary. It will also be understood that, in some embodiments, the body 804 does not include lumens. Thus, in some embodiments, the removed section 806 exposes one or more conductors without exposing one or more lumens.

Figure 8C:
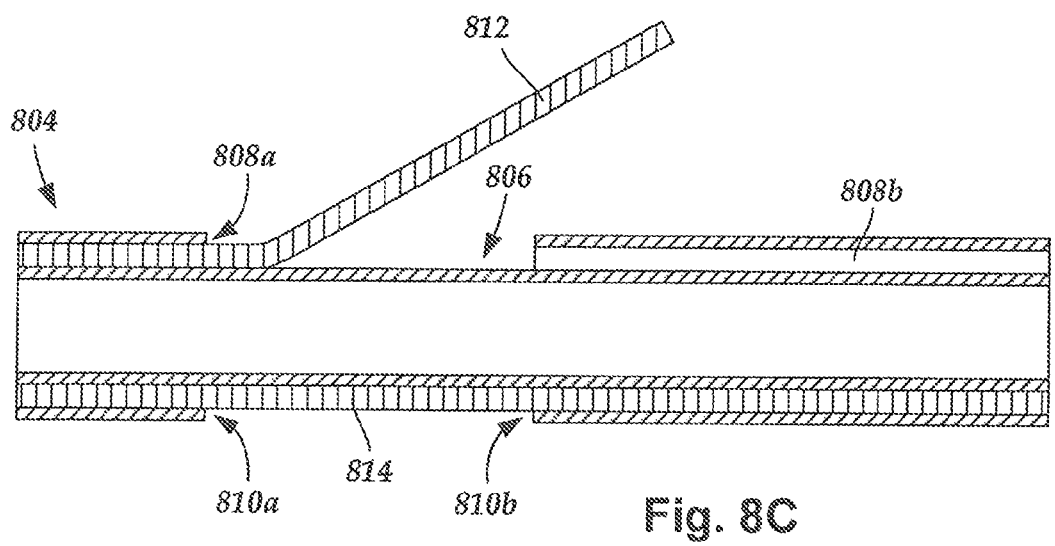
FIG. 8C is a schematic longitudinal cross-sectional view of one embodiment of conductors extending along lumens within a portion of the distal member of FIG. 8B, one end of one of the conductors extending from the distal member at a removed section of the distal member, according to the invention.

FIG. 8C is a schematic longitudinal cross-sectional view of one embodiment of conductors 812 and 814 extending along the lumens 808a and 810a, respectively, of the body 804. The conductor 812 extends from the lumen 808a to the removed section 806 without extending into lumen 808b, while the conductor 814 extends across the entire removed section 806 from the lumen 810a to the lumen 810b. In at least some embodiments, the conductor 814 couples to a connector contact disposed on a connector of the same distal member (e.g., distal member 408 of FIG. 4). In at least some embodiments, the conductor 812 extends to a longitudinally offset distal members (e.g., distal member 406 of FIG. 4) and couples to a connector contact disposed on a connector of the longitudinally offset distal member (e.g., connector contacts 430 of the connector 426 of FIG. 4).

As discussed above, in at least some embodiments the splitter is not an adapter. Hence, in at least some embodiments, the lead (or lead extension) inserted into the connectors 426 and 428 may include terminals that are similar (e.g., in size, shape, orientation, number, or the like) to the terminals 420 disposed on the proximal member. Thus, in at least some embodiments, at least some of the terminals of a lead (or lead extension) inserted into one of the connectors 426 and 428 do not electrically couple to the terminals 420.

For example, in some embodiments, when the proximal member 404 has eight terminals 420, the connectors 426 and 428 are configured and arrange to receive leads (or lead extensions) also having eight terminals. In at least some embodiments, some of the terminals 420 are coupled to the connector 426 and some of the terminals 420 are coupled to the connector 428. For example, in at least some embodiments, four of the terminals 420 are each coupled to one of four connector contacts of the connector 426 and four of the terminals 420 are each coupled to one of four connector contacts of the connector 428. Thus, in at least some embodiments, when an eight-terminal lead (or lead extension) is inserted into one of the four-connector-contact connectors 426 or 428, only four of the eight terminals of the eight-terminal lead (or lead extension) couple to one of the connector contacts.

In at least some embodiments, at least some of the connector contacts disposed in the connectors 426 and 428 are not coupled to one of the conductors. In at least some embodiments, one or more spacers (e.g., dummy contacts) are disposed in the connectors 426 and 428 in lieu of a connector contact not coupled to one of the conductors. It will be understood that the spacers used in lieu of connectors contacts (e.g., dummy contacts) are distinguished from spacers used between adjacent contacts. For example, in at least some embodiments, with reference to FIG. 4, regions 430 and 432 of the connectors 426 and 428, respectively, may include connector contacts that are coupled to terminals 420, while the regions 434 and 436 may include connector contacts that are inactive (e.g., not coupled to a conductor, coupled to a conductor that is not coupled to one of the terminals 429, or the like), or spacers in lieu of connector contacts.

In at least some embodiments, the connector contacts in the connectors 426 and 428 that are coupled to conductors are disposed adjacent to one another within the connector 426 or 428. In at least some embodiments, the connector contacts in the connectors 426 and 428 that are coupled to conductors are separated such that at least two of the connector contacts coupled to conductors are not disposed adjacent to one another within at least one of the connectors 426 or 428. In at least some embodiments, the connector contacts in the connectors 426 and 428 that are coupled to conductors are disposed in a distal end of the connector 426 or 428. In at least some embodiments, the connector contacts in the connectors 426 and 428 that are coupled to conductors are disposed in a proximal end of the connector 426 or 428.

In at least some embodiments, one or more imaging modalities may be used to facilitate or verify proper insertion of a lead (or lead extension) into connectors (e.g., connectors 426 or 428) disposed on distal members (e.g., distal members 406 or 408). In at least some embodiments, spacers between adjacent connector contacts 430 and 432 on the connectors 426 and 428 can be used to facilitate or verify proper insertion of the leads (or lead extensions) into the connectors 426 and 428.

Figure 9A:
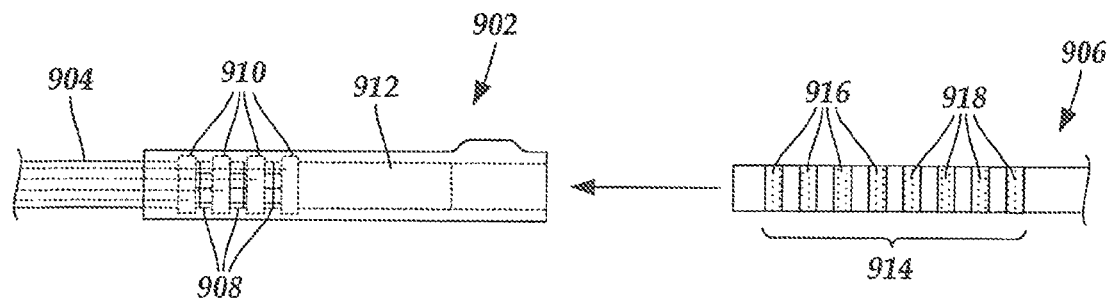
FIG. 9A is a schematic side view of one embodiment of a connector disposed on a distal member and a proximal end of a lead configured and arranged for insertion into the connector, according to the invention.

FIG. 9A is a schematic side view of one embodiment of a connector 902 of a distal member 904 and the proximal end of a lead 906. The connector 902 includes spacers 908 between connector contacts 910 that are coupled to conductors. In at least some embodiments, the connector 902 includes one or more regions 912 that can be formed either as spacers or as inactive connector contacts. In at least some embodiments, the spacers 908 and the region(s) 912 are formed from one or more materials that are transparent to an imaging modality. For example, at least one of the spacers 908 or the region(s) 912 may be formed from one or more materials that are fluoroscopically transparent (e.g., polyurethane, polyetheretherketone, or the like).

In at least some embodiments, the connector 902 includes more connector contacts 910 than regions 912. In at least some embodiments, the connector 902 includes less connector contacts 910 than regions 912. In at least some embodiments, the connector 902 includes the same number of connector contacts 910 and regions 912. It will be understood that, in at least some embodiments a lead extension may be inserted into the connector 902 instead of the lead 906.

In at least some embodiments, the proximal end of the lead 906 includes spaced-apart terminals 914 separated from one another by material that is transparent to the same imaging modality by which the spacers 908 and the region 912 of the connector 902 were transparent (e.g., via fluoroscopy, or the like). When the lead 906 is properly inserted into the connector 902, some of the terminals 914 are configured and arranged to align with the connector contacts 910 that are coupled to conductors, while some of the terminals 914 are configured and arranged to not align with the connector contacts 910. In FIG. 9A, when the lead 906 is properly input to the connector 902, the terminals 916 align with the connector contacts 910 that are coupled to conductors, and the terminals 918 do not align with the connector contacts 910 that are coupled to conductors. In at least some embodiments, the terminals 918 that do not align with the connector contacts 910 align with the region(s) 912.

Figure 9B:
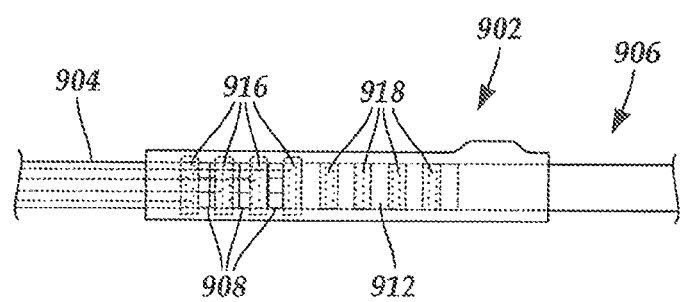
FIG. 9B is a schematic side view of one embodiment of the proximal end of the lead of FIG. 9A inserted into the connector of FIG. 9A, the connector and lead configured and arranged to utilize imaging to facilitate or verify proper insertion of the lead into the connector, according to the invention.

FIG. 9B is a schematic side view of one embodiment of the lead 906 inserted into the connector 902. The terminals 916 are aligned with the connector contacts 910 and the terminals 918 are aligned with the region 912. Accordingly, in at least some embodiments, a health care professional may use an imaging modality to view the connector 902 during insertion (or subsequent to insertion) of the lead 906 and identify when the lead 906 is properly inserted into the connector 902 by alignment of the terminals 916 with the connector contacts 910.

Figure 10:
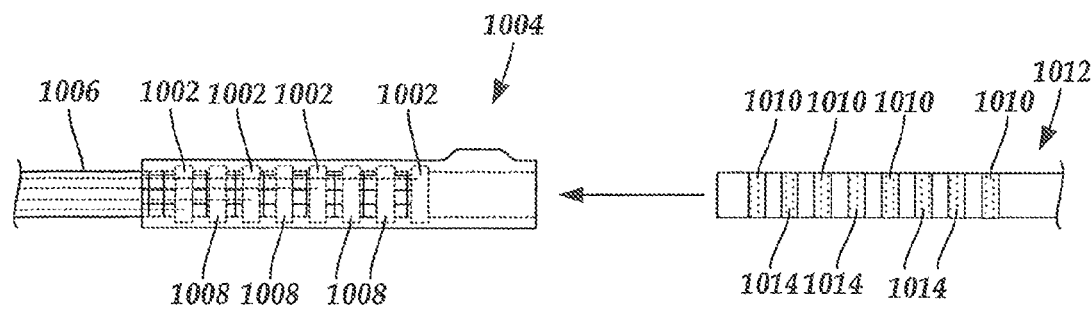
FIG. 10 is a schematic side view of another embodiment of a connector disposed on distal member and a proximal end of a lead configured and arranged for insertion into the connector, according to the invention.

The connector contacts that are coupled to conductors may be arranged along the connector 902 in any configuration. FIG. 10 is a schematic side view of one embodiment of connector contacts 1002 disposed in a connector 1004 of a distal member 1006. The connector contacts 1002 are coupled to conductors disposed along the distal member 1006 and the regions 1008 include at least one contact that is inactive or at least one spacer (see e.g., the region 912 in FIG. 9A). In FIG. 10, when a lead 1012 is inserted into the connector 1004, the connector contacts 1002 are configured and arranged to align with terminals 1010 of the lead 1012, while the regions 1008 are configured and arranged to align with terminals 1014 of the lead 1012.

In at least some embodiments, the connector 1004 includes more connector contacts 1002 than regions 1008. In at least some embodiments, the connector 1004 includes less connector contacts 1002 than regions 1008. In at least some embodiments, the connector 1004 includes the same number of connector contacts 1002 and regions 1008. It will be understood that, in at least some embodiments a lead extension may be inserted into the connector 1004 instead of the lead 1012.

Figure 11:
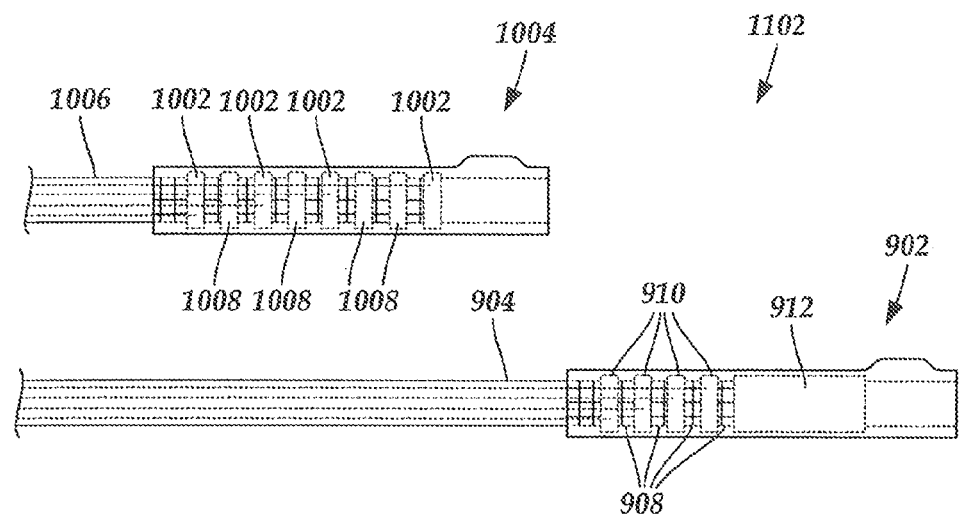
FIG. 11 is a schematic side view of one embodiment of two connectors disposed on distal members of a splitter, one of the connectors being the connector of FIG. 9A and the other of the two connectors being the connector of FIG. 10, according to the invention.

In at least some embodiments, a splitter may include distal members with different configurations of connector contacts disposed in each connector. FIG. 11 is a schematic side view of a distal end of a splitter 1102. The splitter 1102 includes the connectors 902 and 1004 disposed on the distal members 904 and 1006, respectively. As discussed above, the connector contacts 910 are arranged in a configuration that is different from the configuration of the connector contacts 1002. Thus, in at least some embodiments, patient tissue may be stimulated differently by a lead, depending on which connector 902 or 1004 the lead is inserted. It will be understood that splitters may be formed having connectors that are each configured into any configuration of connector contacts coupled to conductors.

Figure 12:
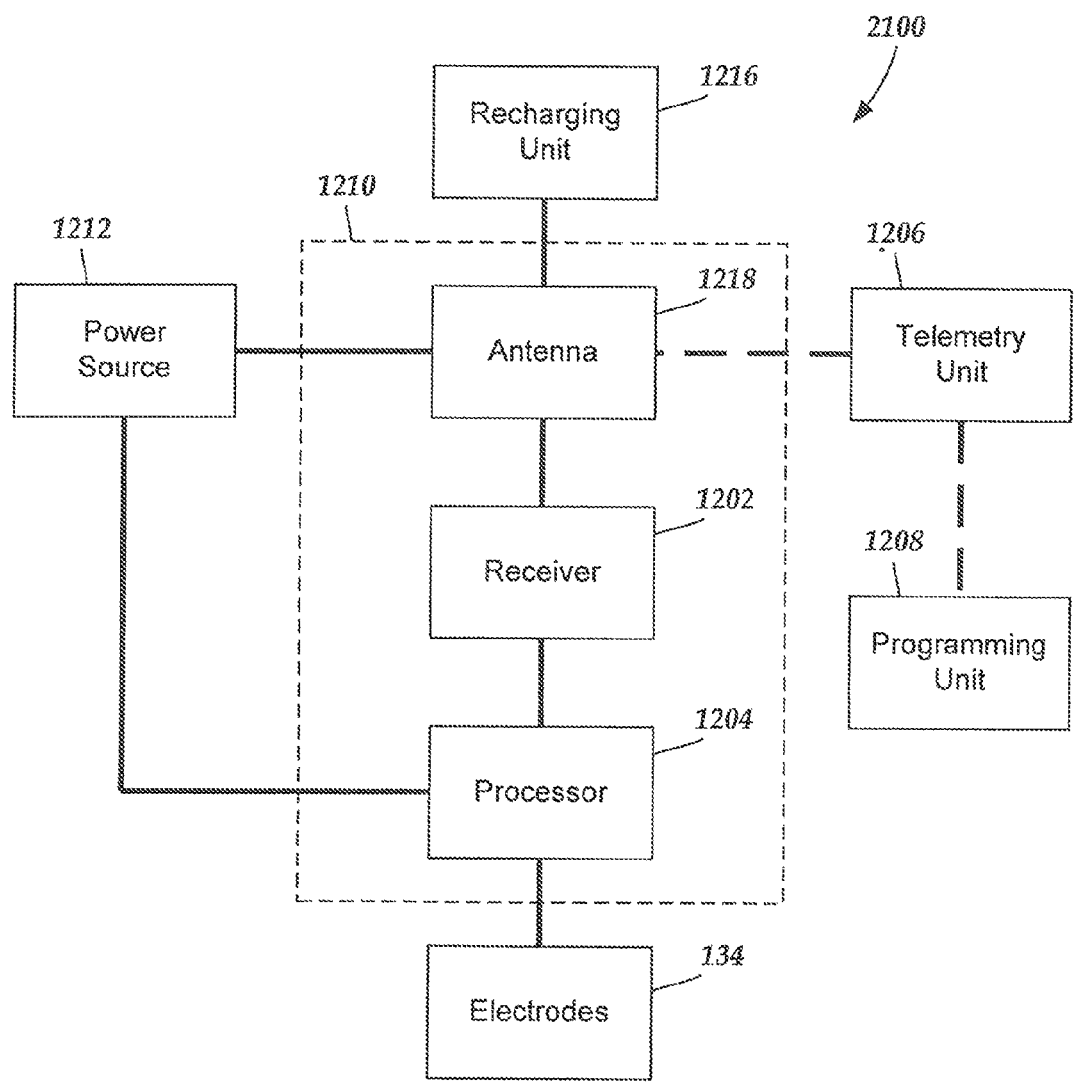
FIG. 12 is a schematic overview of one embodiment of components of an electrical stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for electrically stimulating patient tissue, the method comprising:
    inserting a distal end of at least two leads into a patient, the distal ends of each of the leads comprising a plurality of electrodes;
    coupling proximal ends of each of the leads to a splitter, the splitter comprising a junction having a proximal end and a distal end, an elongated proximal member extending from the proximal end of the junction and comprising a plurality of terminals disposed on a proximal end of the proximal member, and a plurality of elongated distal members extending from the distal end of the junction, each distal member comprising a connector disposed on a distal end of the distal member, at least two of the connectors receiving the proximal ends of the leads inserted into the patient, wherein one of the distal members is longitudinally aligned with the proximal member and at least another one of the distal members is longitudinally offset from the proximal member, and wherein each of a plurality of conductors couple the terminals of the proximal member to the connectors of the distal members, wherein each connector is coupled to a different subset of the terminals using the plurality of conductors, and each terminal of the proximal member is coupled by at least one of the conductors to a connector of only one of the plurality of elongated distal members;
    coupling the terminals disposed on the proximal member of the splitter to a connector of a control module; and
    generating electrical signals by the control module for stimulating patient tissue via the electrodes disposed on each of the at least two leads.

2. The method of claim 1, wherein coupling proximal ends of each of the leads to a splitter comprises coupling proximal ends of each of the leads to a splitter, wherein the distal members of the splitter each define a removed section disposed within a cavity defined in the junction.

3. The method of claim 1, wherein coupling proximal ends of each of the leads to a splitter comprises coupling proximal ends of each of the leads to a splitter, wherein the proximal member of the splitter is coupled to the longitudinally aligned distal member such that the proximal member and that distal member are continuous with one another.

4. The method of claim 1, wherein coupling proximal ends of each of the leads to a splitter comprises coupling proximal ends of each of the leads to a splitter, wherein each of the distal members of the splitter has a different longitudinal length.

5. The method of claim 1, wherein coupling proximal ends of each of the leads to a splitter comprises coupling proximal ends of each of the leads to a splitter, wherein each of the connectors disposed on the distal members of the splitter comprises at least one connector contact coupled to at least one of the conductors.

6. The method of claim 1, wherein coupling proximal ends of each of the leads to a splitter comprises coupling proximal ends of each of the leads to a splitter, wherein the junction of the splitter is h-shaped.

7. The method of claim 1, wherein coupling proximal ends of each of the leads to a splitter comprises coupling proximal ends of each of the leads to a splitter, wherein the splitter comprises two distal members.

8. The method of claim 1, wherein coupling proximal ends of each of the leads to a splitter comprises coupling proximal ends of each of the leads to a splitter, wherein each of the connectors of the splitter is configured and arranged to receive the same type of lead.

9. The method of claim 1, wherein coupling proximal ends of each of the leads to a splitter comprises coupling proximal ends of each of the leads to a splitter, wherein the combined number of connector contacts disposed in each of the connectors of the splitter is equal to the number of the plurality of terminals.

10. A method for electrically stimulating patient tissue, the method comprising:
    inserting a distal end of at least two leads into a patient, the distal ends of each of the leads comprising a plurality of electrodes;
    coupling proximal ends of each of the leads to a splitter, the splitter comprising a junction having a proximal end and a distal end, an elongated proximal member extending from the proximal end of the junction and comprising a plurality of terminals disposed on a proximal end of the proximal member, and a plurality of elongated distal members extending from the distal end of the junction, each distal member comprising a connector disposed on a distal end of the distal member, at least two of the connectors receiving the proximal ends of the leads inserted into the patient, wherein the junction of the splitter is h-shaped, and wherein each of a plurality of conductors couple the terminals of the proximal member to the connectors of the distal members, wherein each connector is coupled to a different subset of the terminals using the plurality of conductors, and each terminal of the proximal member is coupled by at least one of the conductors to a connector of only one of the plurality of elongated distal members;
    coupling the terminals disposed on the proximal member of the splitter to a connector of a control module; and
    generating electrical signals by the control module for stimulating patient tissue via the electrodes disposed on each of the at least two leads.

11. The method of claim 10, wherein coupling proximal ends of each of the leads to a splitter comprises coupling proximal ends of each of the leads to a splitter, wherein the distal members of the splitter each define a removed section disposed within a cavity defined in the junction.

12. The method of claim 10, wherein coupling proximal ends of each of the leads to a splitter comprises coupling proximal ends of each of the leads to a splitter, wherein the proximal member of the splitter is coupled to the longitudinally aligned distal member such that the proximal member and that distal member are continuous with one another.

13. The method of claim 10, wherein coupling proximal ends of each of the leads to a splitter comprises coupling proximal ends of each of the leads to a splitter, wherein the splitter comprises two distal members.

14. A method for electrically stimulating patient tissue, the method comprising:

inserting a distal end of at least two leads into a patient, the distal ends of each of the leads comprising a plurality of electrodes;

coupling proximal ends of each of the leads to a splitter, the splitter comprising a junction having a proximal end and a distal end, an elongated proximal member extending from the proximal end of the junction and comprising a plurality of terminals disposed on a proximal end of the proximal member, and a plurality of elongated distal members extending from the distal end of the junction, each distal member comprising a connector disposed on a distal end of the distal member, at least two of the connectors receiving the proximal ends of the leads inserted into the patient, wherein each of the distal members of the splitter has a different longitudinal length, and wherein each of a plurality of conductors couple the terminals of the proximal member to the connectors of the distal members, wherein each connector is coupled to a different subset of the terminals using the plurality of conductors, and each terminal of the proximal member is coupled by at least one of the conductors to a connector of only one of the plurality of elongated distal members;

coupling the terminals disposed on the proximal member of the splitter to a connector of a control module; and generating electrical signals by the control module for stimulating patient tissue via the electrodes disposed on each of the at least two leads.

15. The method of claim 14, wherein coupling proximal ends of each of the leads to a splitter comprises coupling proximal ends of each of the leads to a splitter, wherein the distal members of the splitter each define a removed section disposed within a cavity defined in the junction.

16. The method of claim 14, wherein coupling proximal ends of each of the leads to a splitter comprises coupling proximal ends of each of the leads to a splitter, wherein the proximal member of the splitter is coupled to the longitudinally aligned distal member such that the proximal member and that distal member are continuous with one another.

17. The method of claim 14, wherein coupling proximal ends of each of the leads to a splitter comprises coupling proximal ends of each of the leads to a splitter, wherein each of the connectors disposed on the distal members of the splitter comprises at least one connector contact coupled to at least one of the conductors.

18. The method of claim 14, wherein coupling proximal ends of each of the leads to a splitter comprises coupling proximal ends of each of the leads to a splitter, wherein the splitter comprises two distal members.

19. The method of claim 14, wherein coupling proximal ends of each of the leads to a splitter comprises coupling proximal ends of each of the leads to a splitter, wherein the junction of the splitter is h-shaped.

20. The method of claim 14, wherein coupling proximal ends of each of the leads to a splitter comprises coupling proximal ends of each of the leads to a splitter, wherein the combined number of connector contacts disposed in each of the connectors of the splitter is equal to the number of the plurality of terminals.

\* \* \* \* \*